(12) United States Patent
Tipler et al.

(10) Patent No.: US 8,247,239 B2
(45) Date of Patent: Aug. 21, 2012

(54) SYSTEM FOR INTRODUCING STANDARD GAS INTO SAMPLE CONTAINER

(75) Inventors: Andrew Tipler, Trumbull, CT (US); Christopher Mazza, Terryville, CT (US); David J. Scott, Willingford (GB)

(73) Assignee: PerkinElmer Health Sciences, Inc., Waltham, MA (US)

( * ) Notice: Subject to any disclaimer, the term of this patent is extended or adjusted under 35 U.S.C. 154(b) by 974 days.

(21) Appl. No.: 11/403,527

(22) Filed: Apr. 13, 2006

(65) Prior Publication Data
US 2006/0263901 A1    Nov. 23, 2006

Related U.S. Application Data

(63) Continuation of application No. PCT/US2004/034793, filed on Oct. 18, 2004.

(60) Provisional application No. 60/481,522, filed on Oct. 17, 2003.

(51) Int. Cl.
*G01N 1/00* (2006.01)
*G01N 30/12* (2006.01)

(52) U.S. Cl. ........ 436/174; 264/259; 264/322; 249/117; 436/106; 436/181; 436/52; 436/161; 422/70; 422/89

(58) Field of Classification Search .................. 436/106, 436/181, 52, 161, 174; 422/70, 89; 264/259, 264/322; 249/117
See application file for complete search history.

(56) References Cited

U.S. PATENT DOCUMENTS

| | | | |
|---|---|---|---|
| 4,180,389 A | 12/1979 | Paul | 55/28 |
| 4,600,559 A | 7/1986 | Hiatt | 422/89 |
| 5,177,995 A | 1/1993 | Risch et al. | 73/23.41 |
| 5,337,619 A | 8/1994 | Hodgins et al. | 73/863.11 |
| 5,646,334 A | 7/1997 | Scheppers et al. | 73/1.06 |
| 5,970,804 A | 10/1999 | Robbat, Jr. | 73/863.12 |
| 5,998,217 A | 12/1999 | Rao et al. | 436/179 |
| 6,162,282 A | 12/2000 | Walters et al. | 95/82 |
| 6,395,560 B1 | 5/2002 | Markelov | 436/181 |
| 6,649,129 B1 | 11/2003 | Neal | 422/89 |
| 6,706,245 B2 | 3/2004 | Neal et al. | 422/100 |
| 2002/0006360 A1 | 1/2002 | Neal et al. | 422/100 |
| 2002/0148353 A1 | 10/2002 | Seeley | 95/86 |

FOREIGN PATENT DOCUMENTS

| | | |
|---|---|---|
| EP | 1 016 364 | 7/2000 |
| WO | WO 94/22009 | 9/1994 |

OTHER PUBLICATIONS

International Search Report & Written Opinion of the International Authority; Jun. 24, 2005; 9 pages.

*Primary Examiner* — Krishnan S Menon
*Assistant Examiner* — Rebecca M Fritchman
(74) *Attorney, Agent, or Firm* — St. Onge Steward Johnston & Reens LLC

(57) ABSTRACT

A method for introducing standard gas into a sample vessel is generally disclosed comprising providing a vessel containing a sample gas and a receptacle with a vessel port, such as sampling needle, pressurizing the vessel with a carrier gas, and introducing a volume of standard gas into the flow path of the carrier gas being used to pressurize the vessel when the vessel port of the receptacle is located within the vessel. In some embodiments, a rotary valve is loaded with the standard gas, and the valve is brought into fluid communication with the flow path of the carrier gas when the vessel port is within the vessel.

16 Claims, 9 Drawing Sheets

SYSTEM FOR INTRODUCING STANDARD GAS INTO SAMPLE CONTAINER

PRIOR APPLICATION

The present application is a continuation of International Patent Application No. PCT/US2004/034793 filed Oct. 18, 2004, which designates the United States, and which claims priority benefits under 35 U.S.C. §119(e) of U.S. Provisional Patent Application Ser. No. 60/481,522, filed Oct. 17, 2003.

FIELD OF THE INVENTION

The present invention relates to a method for introducing standard gas into a sample vessel. More specifically, the invention relates to a method for automatically introducing a volume of standard gas into a vessel containing headspace vapor during sampling.

BACKGROUND OF THE INVENTION

Chromatography is essentially a physical method of separation in which constituents of a test sample in a carrier gas are adsorbed or absorbed and then desorbed by a stationary phase material in a column. A pulse of the sample is introduced into a steady flow of carrier gas, which carries the sample into a chromatographic column. The inside of the column is lined with a liquid, and interactions between this liquid and the various components of the sample—which differ based upon differences among partition coefficients of the elements—cause the sample to be separated into are more or less separated in time. Detection of the gas provides a time-scaled pattern, typically called a chromatogram, that, by calibration or comparison with known samples, indicates the constituents, and the specific concentrations thereof, which are present in the test sample. An example of the process by which this occurs is described in U.S. Pat. No. 5,545,252 to Hinshaw.

Often, the sample is first obtained using a sampling device, which subsequently transfers the sample to the chromatograph. One means of obtaining a sample and introducing it into a chromatographic column is known as "headspace sampling." In conventional headspace sampling, sample material is sealed in a vial and subjected to constant temperature conditions for a specified time. Analyte concentrations in the vial gas phase should reach equilibrium with the liquid and/or solid phases during this thermostatting time. The vial is subsequently pressurized with carrier gas to a level greater than the "natural" internal pressure resulting from thermostatting and equilibration. Then the pressurized vial is connected to the chromatographic column in such a way as to allow for the transfer of a portion of the vial gas phase into the column for a short period of time. An example of such a sampling device is disclosed in U.S. Pat. No. 4,484,483 to Riegger et. al. An example of a chromatographic system employing such a sampling device is disclosed in U.S. Pat. No. 5,711,786 to Hinshaw, which describes using a chromatographic injector between the vial and the chromatographic column.

Often, it is desired to include a known quantity of a known substance—often referred to as an "internal standard"—in the analysis. This internal standard, which contains one or more compounds that are known not to be present in the sample but that are of a similar concentration and chemistry as the sample compounds, can provide reference peaks during the chromatographic analysis to aid peak identification or to improve quantitative precision. For example, in the final chromatographic analysis, the peaks from these standard gas compounds can be identified, quantified, and used to make a ratiometric correction to the quantitative results from the analyte compounds. This technique compensates for instrumental variations that may affect the analytical results, as both the standard gas compound and each analyte are subjected to the same variations, and thus, their relative responses provide a more valid quantitative measure of the amount of analyte present.

For a number of reasons, it can be valuable to introduce the internal standard into the sample vessel itself, prior to the extraction of headspace vapor therefrom. For example, a headspace sampler is typically used to test a number of large number vials in sequence, which are usually held in a rotating carousel or moving rack of some sort. When dealing with a large number of vials in a given autosampling sequence, it is possible for one or more vials to have a leak, which obviously leads to erroneous analytical data. Accordingly, it is advantageous to have the internal standard already present in these vials prior to headspace extraction so that problems with vial integrity may be detected.

Similarly, it is often desired to pre-concentrate the analytes in the sample, and occasionally, remove moisture therefrom, prior to introducing the sample into the chromatographic column. Accordingly, as disclosed in U.S. Pat. Nos. 5,792,423 and 6,395,560 to Markelov, these systems will typically include some kind of "trap" for this purpose, which retains the analytes as they are carried through the trap, and which are later released from the trap, usually by heating, and swept into the chromatographic column. One example is adsorbent traps, which adsorb the analytes and then subsequently desorb those analytes into the chromatographic column, such as the arrangements disclosed in U.S. Pat. No. 5,932,482 to Markelov and U.S. Pat. No. 6,652,625 to Tipler. Accordingly, it is often advantageous to mix the internal standard in with the sample prior to entry into the trap in order to test the trap's efficiency.

A number of systems have been proposed for introducing a standard into a sample vessel. Examples of such arrangements are disclosed in U.S. Pat. No. 6,706,245 to Neal et al. and U.S. Pat. No. 5,998,217 to Rao et al. Each of these systems, however, is somewhat complex, involving multiple transfer lines and complex needle assemblies.

What is desired, therefore, is a system and method for introducing a standard gas into a sample vessel that does not require complicated flow path or needle assemblies. What is further desired is a method for introducing a standard gas into a sample vessel that does not require additional time to perform additional steps.

SUMMARY OF THE INVENTION

Accordingly, an object of the present invention is to provide a method for introducing a standard gas into a sample vessel that utilizes the basic steps for performing headspace sampling to facilitate introduction of the standard.

It is a further object of the present invention to provide a method for introducing a standard gas into a sample vessel that requires minimal modification of, or addition to, the basic hardware required for headspace sampling.

To overcome the deficiencies of the prior art and to achieve at least some of the objects and advantages listed, the invention comprises a method for introducing a standard gas into a sample vessel, including providing a carrier gas inlet for supplying carrier gas, providing a sample vessel holding a sample gas, providing a receptacle adapted to be at least partially inserted into and withdrawn from the vessel, the receptacle having a vessel port, at least partially inserting the receptacle into the vessel, pressurizing the vessel by communicating carrier gas along a flow path from the carrier gas inlet to the vessel port when the vessel port is located within the vessel, and introducing a volume of standard gas into the flow path of the carrier gas as the vessel is being pressurized.

In some of these embodiments, the invention comprises a method for introducing a standard gas into a sample vessel including actuating an internal standard valve to introduce the standard gas into the flow path of the carrier gas.

DETAILED DESCRIPTION OF THE INVENTION

Figure 1:
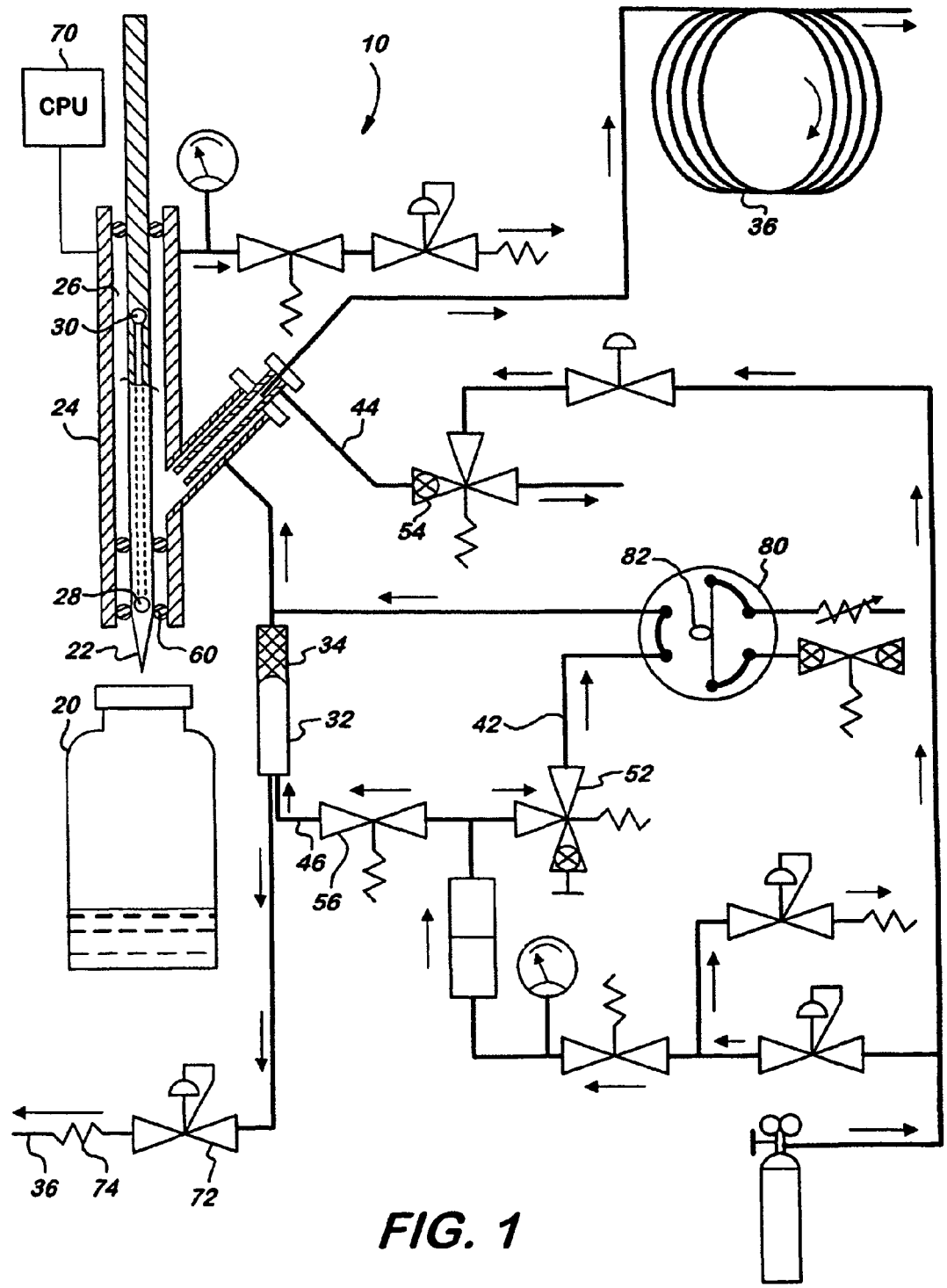
FIG. 1 is a schematic view of a system for performing headspace sampling in accordance with the invention in standby mode.

The basic components of one embodiment of a system for introducing standard gas into a sample vessel in accordance with the invention are illustrated in FIG. 1. As used in the description, the terms "top," "bottom," "above," "below," "over," "under," "above," "beneath," "on top," "underneath," "up," "down," "upper," "lower," "front," "rear," "back," "forward" and "backward" refer to the objects referenced when in the orientation illustrated in the drawings, which orientation is not necessary for achieving the objects of the invention.

As illustrated in FIG. 1, which shows the system 10 in standby mode, a sampling device, such as a headspace sampler, holds a plurality of vessels (i.e., headspace vials) 20 that contain the sample to be extracted and analyzed. Typically, the headspace sampler includes a receptacle 22, such as a sampling needle, disposed in a sampling head 24, and the needle 22 is adapted to be partially inserted into and withdrawn from the vessels 20. The sampling head 24 has a sample chamber 26, and the sampling needle 22 has a vessel port 28 through which fluid is communicated between the needle 22 and the interior of the vials 20 and a sample chamber port 30 through which fluid is communicated between the needle 22 and the sample chamber 26.

An adsorbent housing 32 having an adsorbent 34 disposed therein (commonly referred to as an adsorbent trap), a flow controller 72, a fixed restrictor 74, and a vent 36 are in fluid communication with the sample chamber 26. Accordingly, when headspace vapor is extracted from a vial 20 and mixes with a carrier gas, this sample mixture can flow through the adsorbent 34, which will adsorb the analytes to be measured, and out the vent 36 to the atmosphere. In certain advantageous embodiments, the adsorbent 34 is hydrophobic, thereby allowing moisture to be easily purged from the system by carrier gas, as further explained below. The adsorbent 34 may include any material suitable for this purpose, such as, for example, graphitized carbon black, a polymeric adsorbent, or a carbon molecular sieve.

The adsorbent housing 32 is in fluid communication with a gas chromatograph, the basic components of which are a chromatographic column 36 and a detector (not shown). Accordingly, analytes that have been adsorbed by the adsorbent 34 can be desorbed into the column 36. For this reason, in certain advantageous embodiments, the adsorbent housing 32 is temperature controllable, and thus, the adsorbent 34 can be heated to desorb the analytes retained by the adsorbent 34 before a carrier gas sweeps them out of the housing 32 and into the column 36.

A plurality of gas inlets are provided to supply and control fluid flowing throughout the system 10. For example, the system includes a first carrier gas inlet 42 for generally providing carrier gas needed by the system. For instance, the inlet 42 may provide carrier gas to different parts of the system 10 at different stages of operation, such as, for example, by providing the sampling head 24 with fluid to pressurize the vessel 20, or, as another example, by providing carrier gas to the adsorbent housing 32 to carry a sample containing analytes thereto or to sweep away moisture contained therein. The system 10 also has a second gas inlet 44 for providing gas that may be used by various parts of the system at various stages, but primarily for isolating the chromatographic column 36 from the rest of the system in order to prevent contaminated fluid from entering the column 36 until it is specifically desired to desorb the analytes thereinto. The system also includes a third inlet 46, primarily for providing carrier gas to the adsorbent housing 32 in order to sweep analytes into the column 36 as the analytes are desorbed from the adsorbent 34. Valves 52, 54, 56 are provided to open and close inlets 42, 44, 46, respectively.

Figure 4:
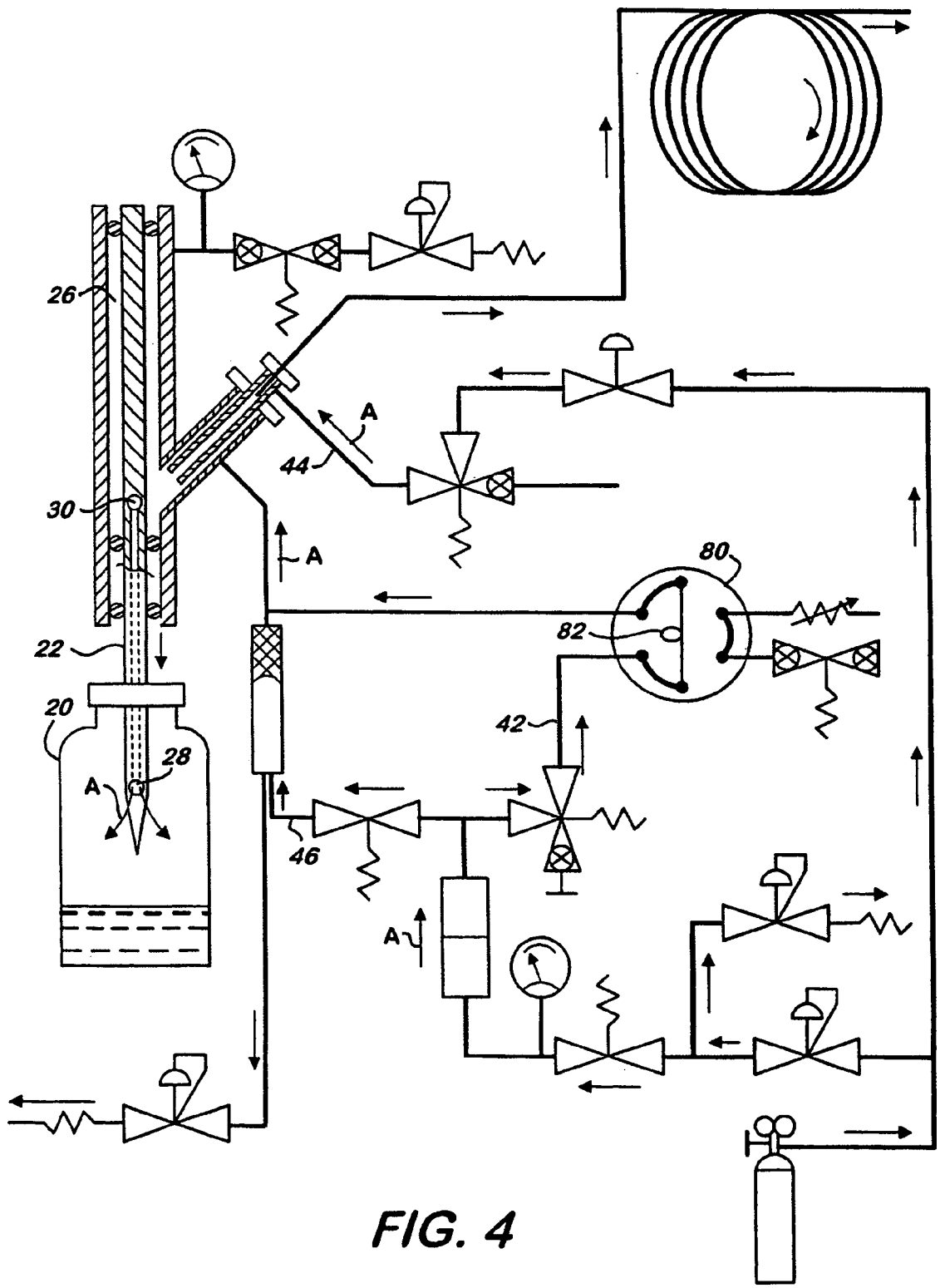
FIG. 4 is a schematic view of the system for performing headspace sampling of FIG. 1 during the vessel pressurization/standard addition stage.

A valve 80 is provided for introducing a standard gas into the system. The valve may, for example, comprise a six port gas sampling valve that includes a sampling loop 82. Accordingly, the valve 80 can be rotated such that the loop 82 can be alternately placed in-line with the flow of a standard gas and the flow of the carrier gas in the system, as shown in FIGS. 1 and 4, and as further described below. As a result, the loop 82 can alternately receive standard gas from a standard gas source and discharge standard gas into the carrier gas flow of the system.

Figure 2:
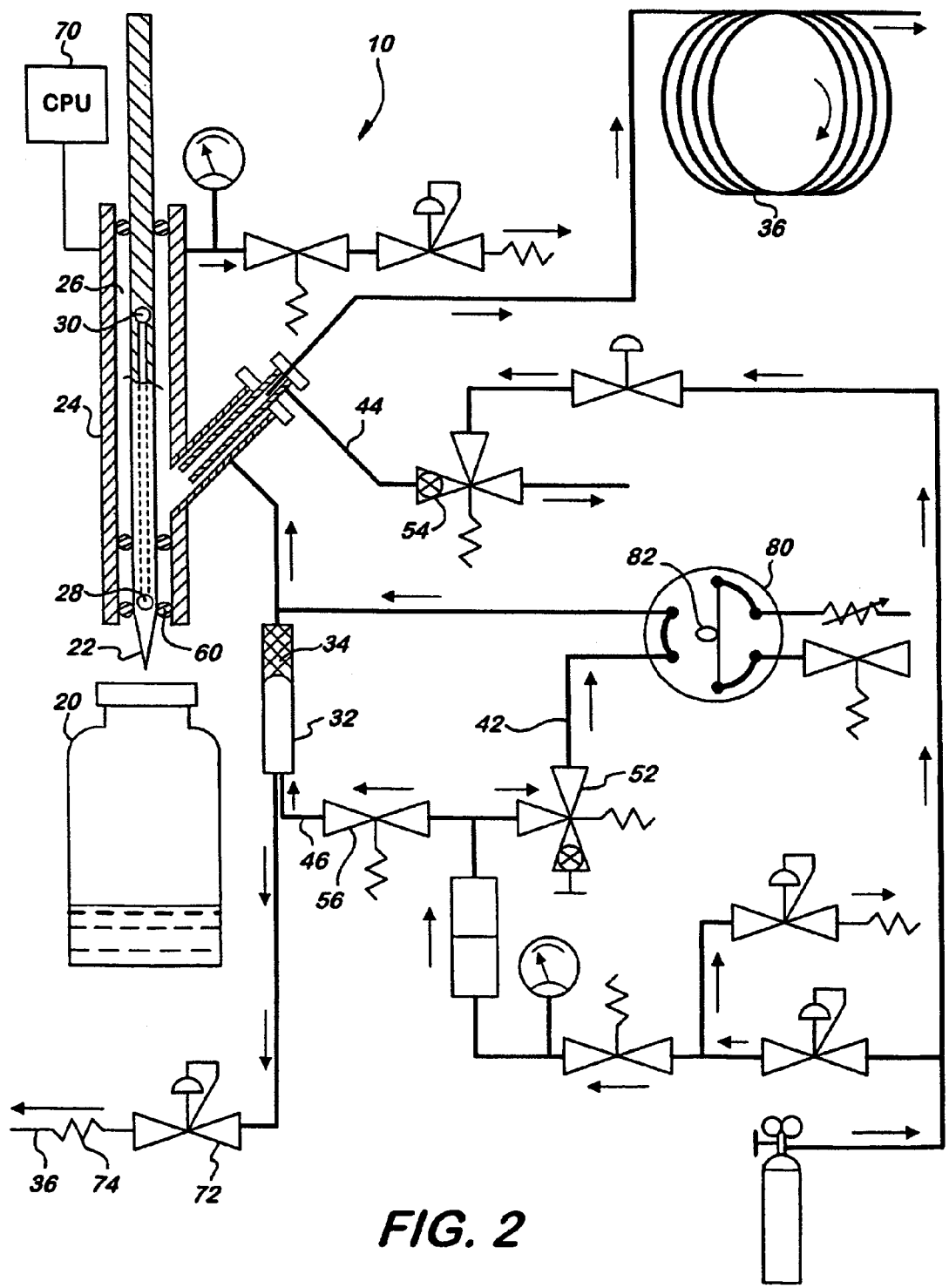
FIG. 2 is a schematic view of a system for performing headspace sampling in accordance with invention in the loop load stage.

Operation of the above described assembly is illustrated stepwise in FIGS. 2-8. A loop load step is illustrated in FIG. 2. The valve 80 is positioned such that the loop 82 is not in-line with the flow of carrier gas entering from inlet 42. Instead the valve, which is illustrated in more detail in FIGS. 9A-C, is positioned such that the loop 82 is in communication with a standard gas source 84 via a valve 86. In this way, a volume of standard gas is loaded into the loop 82.

After the loop 82 is loaded with the standard gas, the valve 86 is closed, such that the system is essentially returned to the standby mode illustrated in FIG. 1. At this point, the pressure in the loop is equilibrated, which can be performed in any of the ways illustrated in FIGS. 9A-C. For example, as illustrated in FIG. 9A, standard gas from the loop 82 can simply be discharged through the needle valve 88 and into a vessel 90 containing a liquid. As shown in FIG. 9B, in other embodiments, in order to reduce variations that may be caused by changes in atmospheric pressure, a classical liquid manometer 92 may be used instead of the vessel 90. As illustrated in FIG. 9C, in still other embodiments, in order to achieve a very fast equilibration time, a back-pressure regulator 94 may be employed to provide an appropriate constant back-pressure inside the loop 82.

Figure 3:
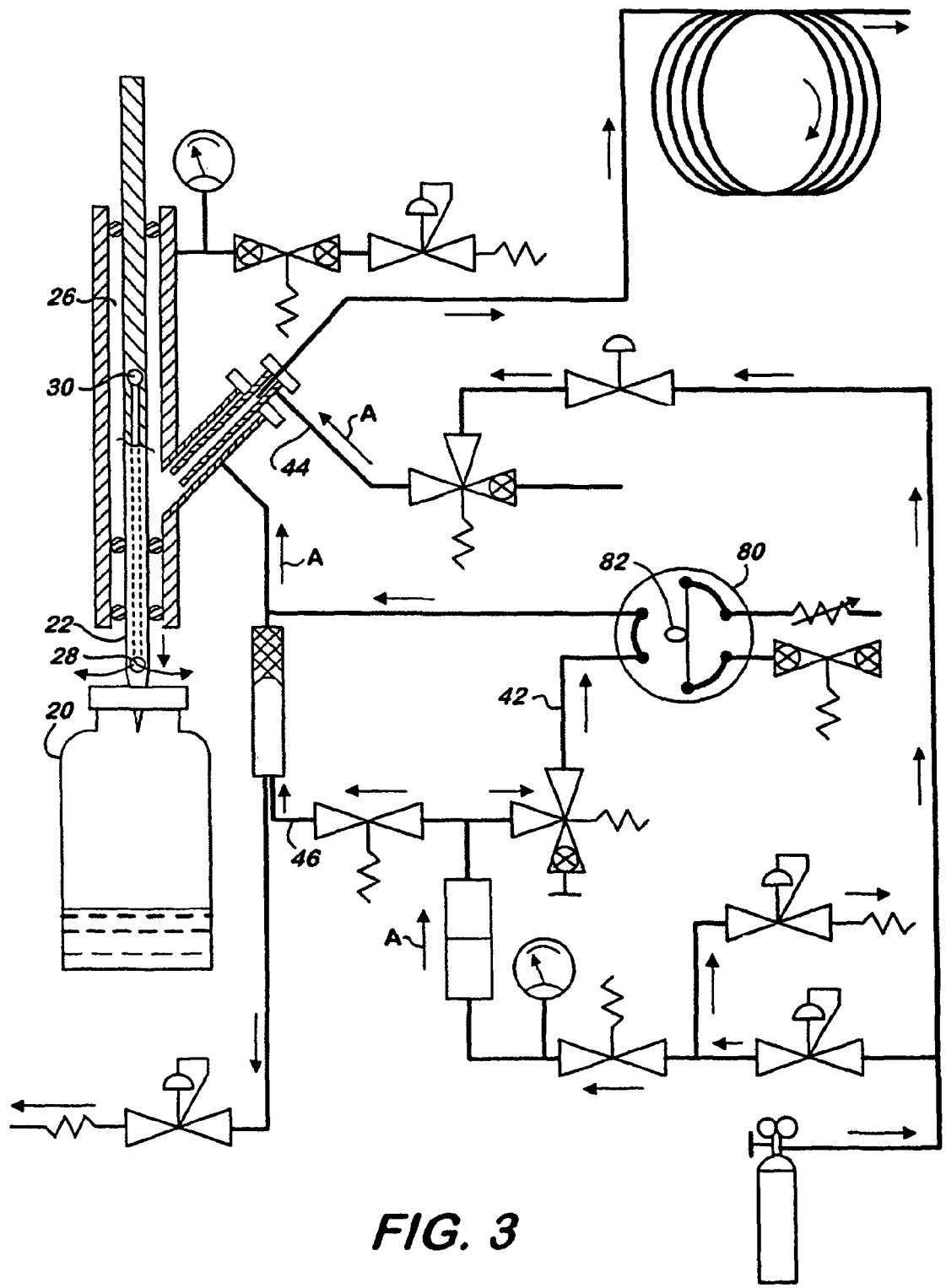
FIG. 3 is a schematic view of the system for performing headspace sampling of FIG. 1 during the vessel penetration stage.

A vessel penetration step is illustrated in FIG. 3. The sampling needle 22 begins to lower into the vial 20, puncturing the septum thereof as it does so. As the vessel port 28 exits the sampling head 24 and becomes exposed to ambient air, carrier gas escapes to the atmosphere. Accordingly, the sample loop 82 remains off-line until the appropriate time, as further described below.

A pressurization and standard addition step is illustrated in FIG. 4. As shown therein, the sampling needle 22 further descends into the vial 20, bringing the vessel port 28 into fluid communication with the interior of the vial 20. The inlets 42, 44, 46 are all opened, sending carrier gas into the sample chamber 26, through the chamber port 30, down through the needle 22, and into the vial 20 (indicated by arrows A). In this way, the vial is pressurized. Because the vessel port 28 is now in fluid communication with the interior of the vial 20, the valve 80 is actuated, causing the sample loop 82 to be brought in-line with the flow path of the carrier gas flowing towards the vial 20 in order to pressurize same. Accordingly, as the carrier gas flows towards the vial 20, it sweeps the standard gas in the loop 82 along with it into the sampling needle 22 and vial 20.

Figure 5:
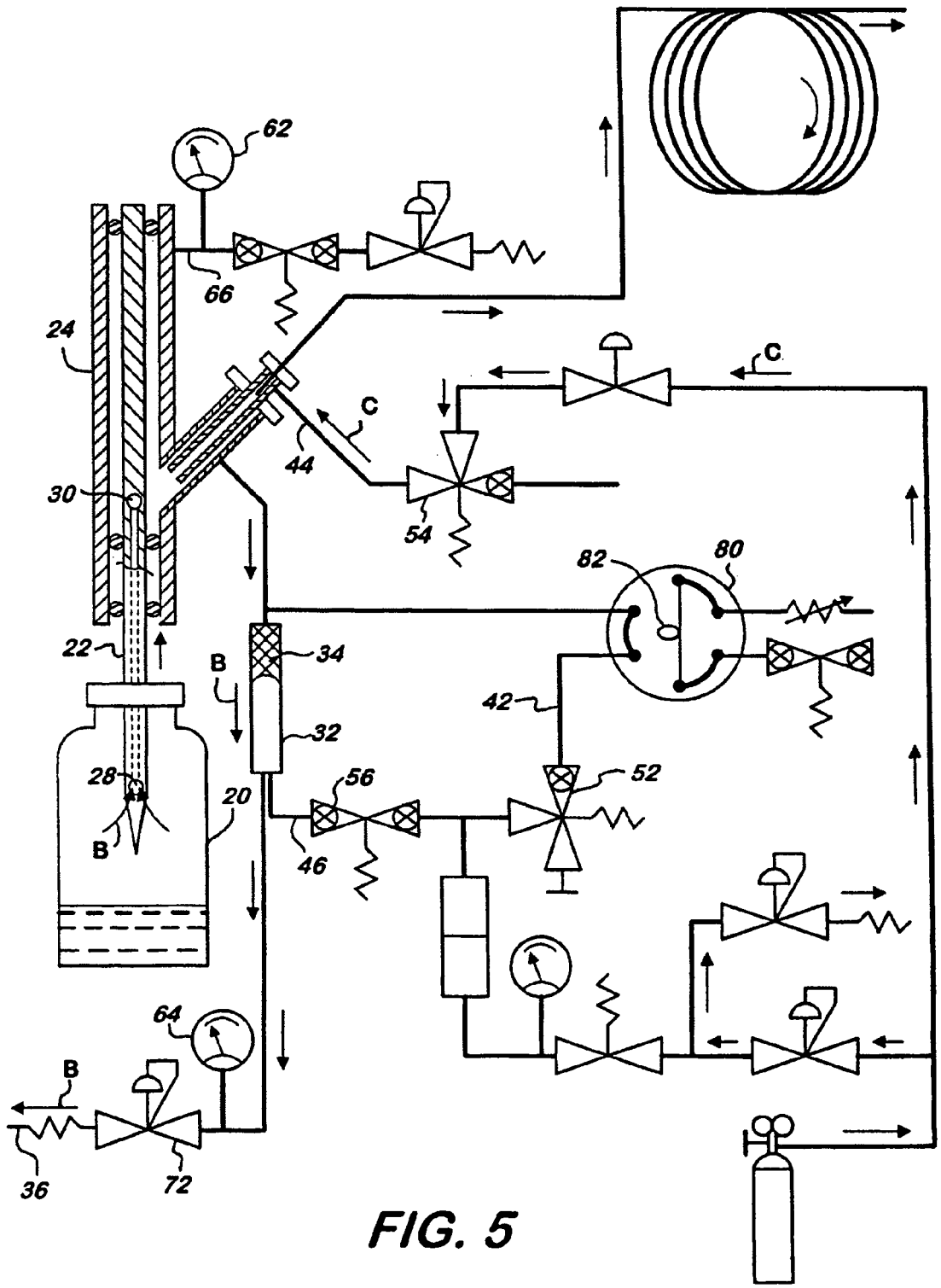
FIG. 5 is a schematic view of the system for performing headspace sampling of FIG. 1 during the venting (trap load) stage.

A venting (or trap load) step is illustrated in FIG. 5. As shown therein, the inlet valve 52 is closed, terminating the supply of fluid from the inlet 42. Likewise, the valve 56 terminates the supply of fluid from inlet 46. As a result, fluid containing the analytes to be measured elutes from the vial 20 through the vessel port 28, through the needle 22, out the chamber port 30, through the adsorbent housing 32, where the adsorbent 34 adsorbs the analytes, and out through the vent 36. (indicated by arrows B). The inlet valve 54 remains open, allowing fluid to continue to enter through the inlet 44 and isolate the column 36 (indicated by arrows C). The valve 80 is returned to its original position, such that the loop 82 is no longer in line with flow path of the carrier gas, and remains ready to be again loaded with standard gas as previously described.

Because the pressure in the vial 20 is proportional to the amount of sample in the vial 20, the pressure drops as the headspace vapor elutes from the vial 20, which normally causes the rate of flow to gradually decrease during the venting process. Accordingly, in certain advantageous embodiments, a flow controller 72 is provided to counter this result, which, in response to the gradual decrease in pressure, gradually increases the flow therethrough, effectively increasing the rate of flow as the depletion of the headspace vapor in the vial 20 decreases the rate of flow. In certain advantageous embodiments, the flow controller 72 is configured to increase flow in an amount directly proportional to the decrease in pressure, thereby maintaining a constant flow rate. In this way, the process of extracting headspace vapor from the vial 20 does not immediately begin gradually slowing down as the venting stage proceeds, thereby resulting in quicker extraction times. In some embodiments, the flow controller 72 comprises a forward pressure regulator. However, in other embodiments, the flow controller may comprises any device suitable for controlling flow therethrough, such as, for example, a mass flow controller or an electronic flow controller.

The aforementioned steps of pressurizing the sample vial 20 and venting the headspace therein through the adsorbent housing 32 and out the vent 36, however, does not extract all of the headspace from the vial 20. Instead, a certain percentage of the original headspace vapor remains in the vial 20 at atmospheric pressure. Therefore, in certain advantageous embodiments, multiple pressurization/venting cycles are performed. Because the amount of time expended to perform a pressurization-venting cycle is significantly decreased due to the use of the flow controller 72 to maintain a constant flow rate, it is possible to perform multiple cycles in succession. Typically a processor 70 automatically controls the amount of pressurization-venting cycles that are performed. Accordingly, an operator of the system 10 can determine how many cycles are desired by deciding upon an appropriate balance between the amount of vapor to be extracted and the amount of time to be expended performing additional cycles, and the operator can then input this value to the processor 70. Alternatively, the operator can determine what percentage of residual vapor is acceptable and input this value to the processor 70, which can then calculate the minimum number of pressurization-venting cycles required. The number of pressurization-venting cycles input by the operator, or calculated by the processor 70, are then performed successively before the system 10 proceeds to perform the remaining steps discussed below.

In certain advantageous embodiments, the system 10 includes a gauge for determining the pressure in the headspace vial 20. Though this may be any device capable of measuring the pressure in the vial 20 and communicating this information to either the system or an operator of the system, in certain embodiments, this gauge is a pressure transducer 62 in fluid communication with the vial 20. Accordingly, as the carrier gas carrying the headspace vapor flows past the transducer 62, the operator may be promptly alerted upon detection of an undesirable condition in the vial 20 by, for example, an LED, an audible alarm, or a log report or profile on a visual display screen.

Because the rate of flow remains constant due to the use of the flow controller 72, various undesirable conditions can be easily detected by monitoring the pressure with the transducer 62, such as a leak in the vial, an incorrect starting pressure, an defective vial resulting in abnormal vial capacity, or the presence of too much or too little sample in the vial. As noted above, the drop in pressure is proportional to the amount of sample flowing out of the vial 20. Because vent time is normally proportional to both the sample volume in the vessel and the pressure, a plot of the pressure decay over time generally results in an exponential profile, making measurement and comparison of the pressure decays somewhat difficult. However, because the flow controller 72 maintains a constant flow rate, a plot of the pressure decay over time results in a linear profile. Therefore, measurement of the pressure decay is very useful in determining whether the vial has a leak or other undesired condition.

The transducer 62 may be located anywhere suitable for measuring the pressure prior to the influence of a flow controller. For example, in some embodiments, the transducer may be positioned in the flow path immediately preceding the flow controller 72. However, in certain advantageous embodiments, a position proximate to the sampling head 24 is used, such as the position of pressure transducer 62 located at the needle purge 66, in order to avoid possible external factors from effecting an accurate measurement of the pressure, such as, for example, a slight pressure drop across the adsorbent 34.

Figure 6:
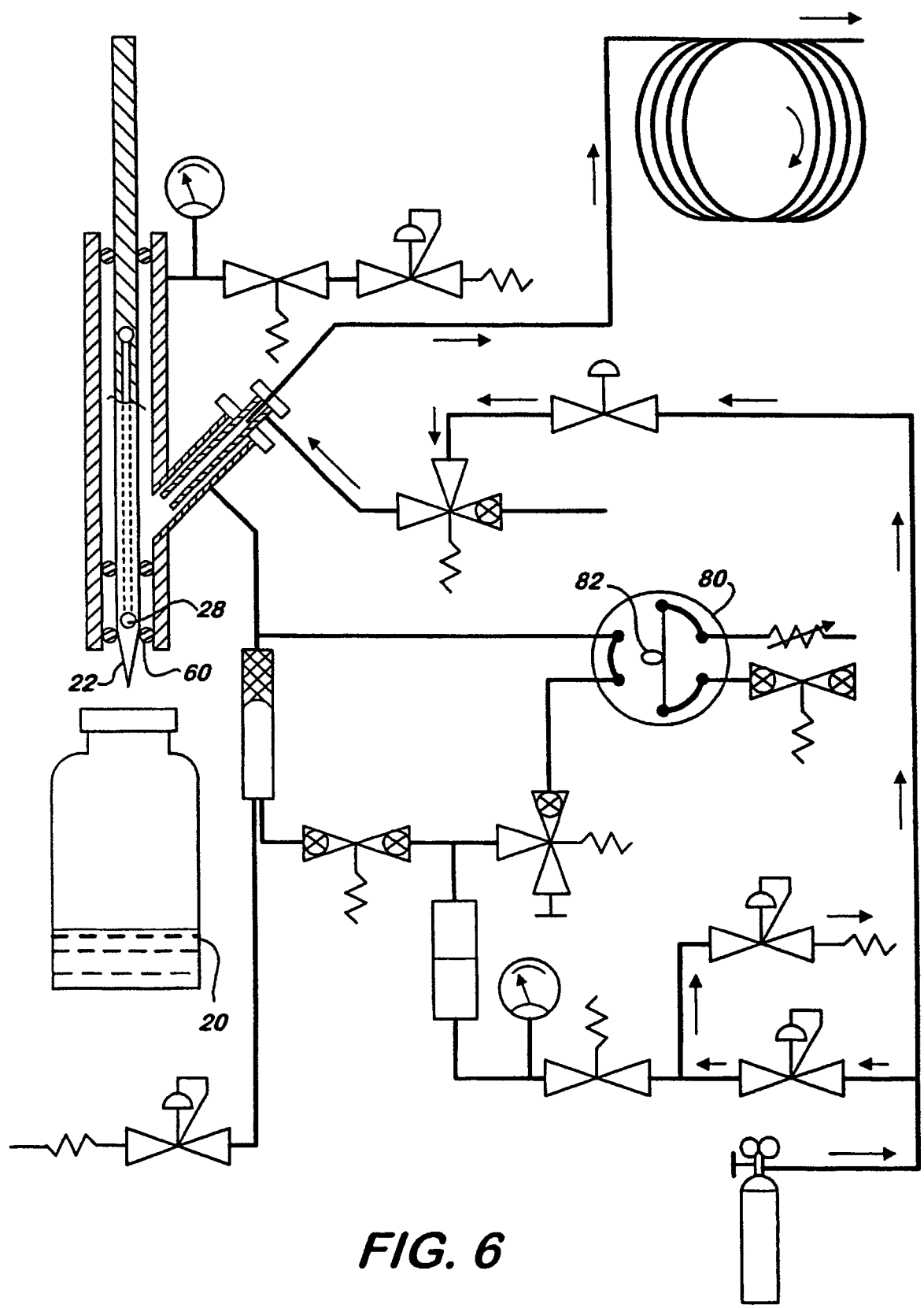
FIG. 6 is a schematic view of the system for performing headspace sampling of FIG. 1 during the needle withdrawal stage.
Figure 7:
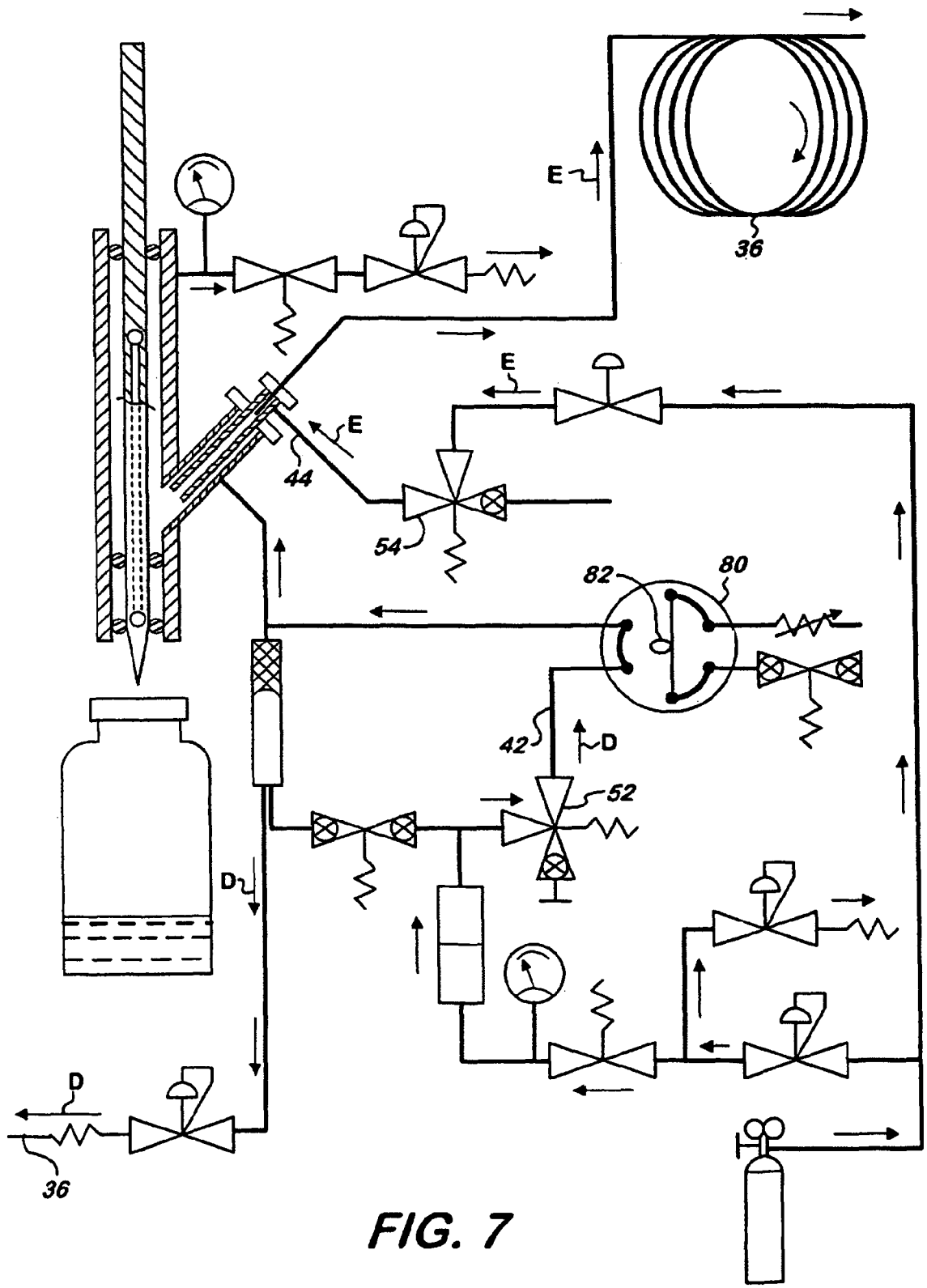
FIG. 7 is a schematic view of the system for performing headspace sampling of FIG. 1 during the trap purge stage.

Next, in embodiments where a significant amount of moisture is present in the sample being analyzed, a dry purge step may be desired. As shown in FIG. 6, the needle 22 is first withdrawn from the vial 20, bringing the vessel port 28 above the seal 60. Next, as illustrated in FIG. 7, the inlet valve 52 is opened again, thereby allowing fluid to once again enter the system via the inlet 42. The fluid flows down into the adsorbent housing 32, sweeping any moisture therein out through the vent 36 (indicated by arrows D). Once again, the inlet valve 54 remains open, allowing fluid to continue to enter through the inlet 44 and isolate the column 36 (indicated by arrows E).

Figure 8:
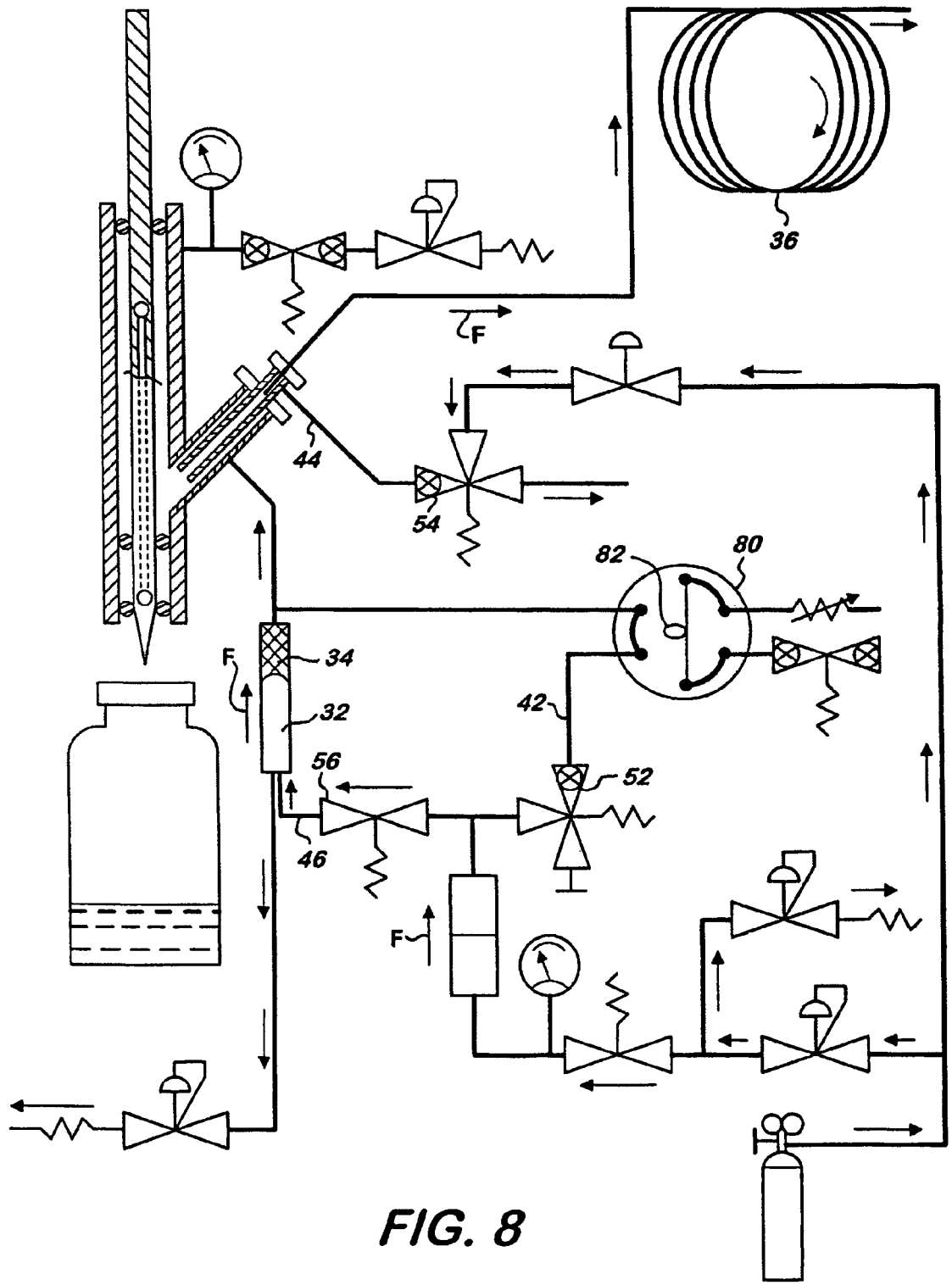
FIG. 8 is a schematic view of the system for performing headspace sampling of FIG. 1 during the trap desorption stage.
Figure 9A:
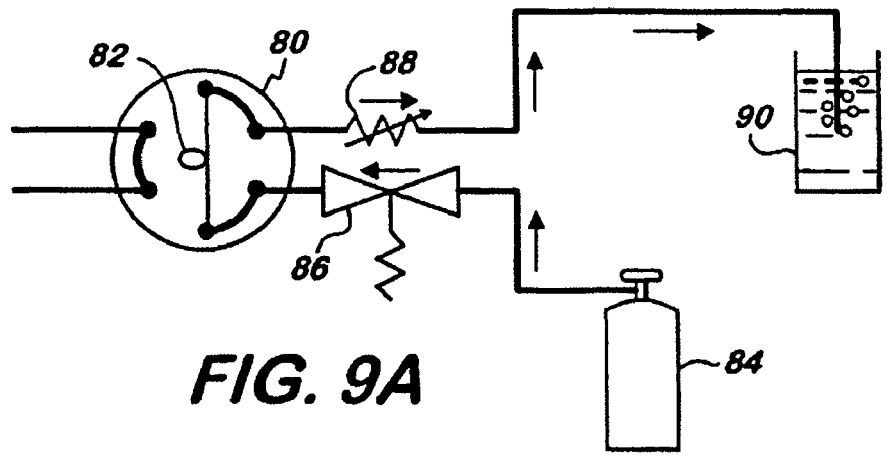
FIG. 9A is schematic view of the sampling loop of FIG. 1 during pressure equilibration.
Figure 9B:
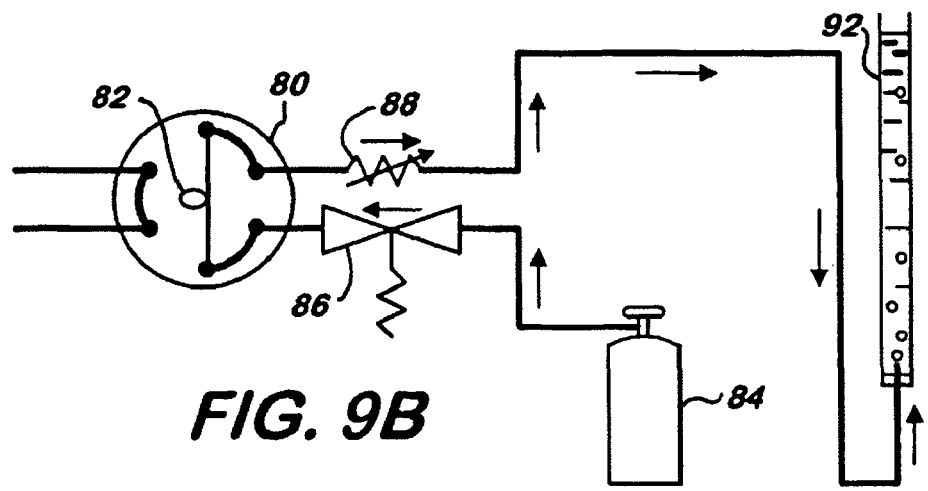
FIG. 9B is schematic view of the sampling loop of FIG. 1 during pressure equilibration.
Figure 9C:
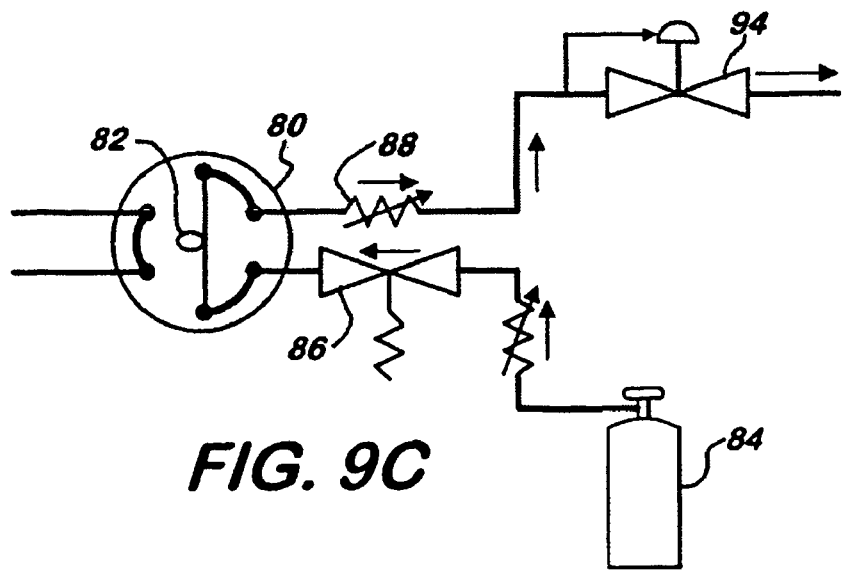
FIG. 9C is schematic view of the sampling loop of FIG. 1 during pressure equilibration.

A desorption step is illustrated in FIG. 8. As shown therein, the valves 52, 54 are closed, terminating the supply of fluid from inlets 42, 44. The valve 56 is opened, allowing fluid to flow in through inlet 46. The adsorbent housing 32 is heated to desorb the analytes retained by the adsorbent 34. Carrier gas enters through the inlet 46 and flows into the adsorbent housing 32, sweeping the desorbed analytes into the chromatographic column 36 (indicated by arrows F).

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method for introducing standard gas into a sample vessel, comprising:
    providing a carrier gas inlet for supplying carrier gas;
    providing a sample vessel holding a sample gas;
    providing a sampling head having a sample chamber;
    providing an internal standard valve;
    providing a receptacle disposed in the sampling head, the receptacle adapted to be at least partially inserted into and withdrawn from the vessel, the receptacle having a vessel port, a sample chamber port and a seal;
    purging the receptacle by bringing the vessel port above the seal and opening the internal standard valve;
    at least partially inserting the receptacle into the vessel when the vessel is holding the sample gas;
    pressurizing the vessel by communicating carrier gas along a flow path from the carrier gas inlet to the vessel port when the vessel port is located within the vessel;
    introducing a volume of standard gas into the flow path of the carrier gas and into the sample vessel as the vessel is being pressurized; and
    extracting the sample, the carrier gas, and the standard gas from the vessel,
    communicating the sample gas, carrier gas, and standard gas extracted from the vessel through an adsorbent, which adsorbs analytes in the sample gas and the standard gas, and out a vent,
    wherein the step of introducing the volume of standard gas into the flow path of the carrier gas occurs prior to the step of extracting the sample, the carrier gas, and the standard gas from the vessel, and
    wherein the step of introducing a volume of standard gas into the flow path of carrier gas comprises actuating the internal standard valve.

2. The method of claim 1, wherein:
    the internal standard valve includes a valve loop; and
    the step of actuating the valve comprises placing the valve loop in-line with the flow path of the carrier gas.

3. The method of claim 2, further comprising the step of loading the valve loop with the volume of standard gas prior to the step of actuating the valve.

4. The method of claim 3, further comprising the step of equilibrating the pressure in the valve loop prior to the step of introducing the volume of standard gas into the flow path of the carrier gas.

5. The method of claim 4, wherein the step of equilibrating the pressure in the valve loop includes the steps of:
    determining an equilibration time;
    discharging some of the standard gas loaded into the valve loop through a needle valve for the determined equilibration time.

6. The method of claim 4, wherein the step of equilibrating the pressure in the valve loop includes the step of discharging some of the standard gas loaded into the valve loop into a vessel containing liquid.

7. The method of claim 4, wherein the step of equilibrating the pressure in the valve loop includes the step of discharging some of the standard gas loaded into the valve loop into a liquid manometer.

8. The method of claim 4, wherein the step of equilibrating the pressure in the valve loop includes the step of discharging some of the standard gas loaded into the valve loop through a back-pressure regulator.

9. The method of claim 1, wherein the sample vessel includes a septum, wherein the receptacle comprises a sampling needle having a tip at its lower end for puncturing the septum, and wherein the vessel port comprises an orifice located in a lower portion of the needle.

10. A system for introducing standard gas into a sample vessel, comprising:
    a sampling head having a sample chamber, and
    a receptacle, the receptacle disposed in the sampling head, the receptacle adapted to be inserted into and withdrawn from a sample vessel, said receptacle having a vessel port for communicating carrier gas into the vessel when the vessel contains a sample gas and said receptacle in inserted thereinto and a sample chamber port through which fluid is communicated between the receptacle and sample vessel;
    a carrier gas inlet for supplying a carrier gas flow, the carrier gas pressurizing the vessel;
    a conduit through which the carrier gas flow is communicated from said carrier gas inlet to said receptacle;
    a valve moveable from an unactuated position to an actuated position when said receptacle is inserted into the sample vessel containing the sample gas, wherein said valve supplies a standard gas into the carrier gas flow and into the sample vessel when in the actuated position,
    wherein said receptacle comprises a sampling needle having a tip at its lower end, and wherein the vessel port comprises an orifice located in a lower portion of said needle.

11. The system of claim 10, wherein said valve includes a valve loop, wherein, when said valve is in the actuated position, said valve loop is in-line with the carrier gas flow.

12. The system of claim 11, wherein the standard gas is loaded in said valve loop.

13. A system for introducing standard gas into a sample vessel, comprising:
    a carrier gas inlet for supplying a carrier gas;
    a sampling head, the sampling head having a sample chamber;
    a receptacle, the receptacle disposed in the sampling head, the receptacle adapted to be inserted into and withdrawn from a sample vessel containing a sample gas, said receptacle having a vessel port and a sample chamber port;

a conduit through which the carrier gas flows from said carrier gas inlet to said receptacle and into the sample vessel, the carrier gas pressurizing the vessel;

a valve that, when in an actuated position, supplies an internal standard gas into said conduit, wherein said receptacle comprises a sampling needle having a tip at its lower end, and wherein the vessel port comprises an orifice located in a lower portion of said needle.

14. The system of claim 13, wherein said valve includes a valve loop, wherein, when said valve is in the actuated position, said conduit comprises said valve loop.

15. The system of claim 14, wherein the internal standard gas is loaded in said valve loop.

16. The method of claim 1, further comprising the step of causing the sample gas and the internal standard to elute from the sample vessel through the vessel port by interrupting the flow of carrier gas to the vessel port when the vessel port is located within the vessel.

* * * * *

UNITED STATES PATENT AND TRADEMARK OFFICE
CERTIFICATE OF CORRECTION

| | | |
|---|---|---|
| PATENT NO. | : 8,247,239 B2 | Page 1 of 1 |
| APPLICATION NO. | : 11/403527 | |
| DATED | : August 21, 2012 | |
| INVENTOR(S) | : David J. Scott | |

It is certified that error appears in the above-identified patent and that said Letters Patent is hereby corrected as shown below:

On the Title Page, Item 75 should read:

Item (75) Inventors: David J. Scott, Wallingford, CT (US)

Signed and Sealed this
Twenty-third Day of October, 2012

David J. Kappos
*Director of the United States Patent and Trademark Office*